United States Patent

Albrecht et al.

[11] Patent Number: 4,831,130
[45] Date of Patent: May 16, 1989

[54] β-LACTAM ANTIBACTERIAL AGENTS

[75] Inventors: Harry A. Albrecht, Towaco; Frederick M. Konzelmann, West Paterson; Dennis D. Keith, Montclair, all of N.J.

[73] Assignee: Hoffmann-La Roche Inc., Nutley, N.J.

[21] Appl. No.: 71,846

[22] Filed: Jul. 10, 1987

Related U.S. Application Data

[63] Continuation of Ser. No. 615,607, May 31, 1984, abandoned.

[51] Int. Cl.$^4$ .................. A61K 31/42; A61K 31/425; C07D 417/14; C07D 413/12
[52] U.S. Cl. ..................... 540/363; 540/364
[58] Field of Search .................. 540/363, 364

[56] References Cited

U.S. PATENT DOCUMENTS 4,587,047  5/1986  Breuer ........................... 540/363

FOREIGN PATENT DOCUMENTS 62876  10/1982  European Pat. Off. .

Primary Examiner—Mark L. Berch
Attorney, Agent, or Firm—Jon S. Saxe; Bernard S. Leon; Richard J. Mazza

[57] ABSTRACT

Compounds of the formula

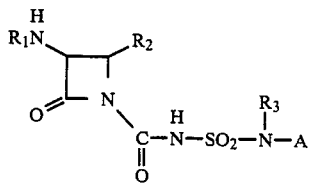

wherein A is one of the following:

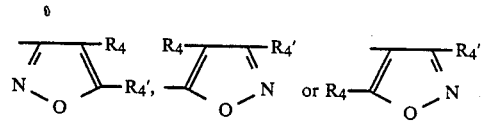

in which $R_1$, is acyl, $R_2$ is hydrogen, lower alkyl, lower alkoxycarbonyl or aminocarbonyl, $R_3$ is hydrogen or lower alkyl and $R_4$ and $R_4'$ are hydrogen, lower alkyl, lower alkoxy, acyl or aralkyl, as well as pharmaceutically acceptable salts of such compounds, are useful as antibacterial agents.

30 Claims, No Drawings

β-LACTAM ANTIBACTERIAL AGENTS

This is a continuation of application Ser. No. 615,607, filed May 31, 1984, now abandoned.

β-LACTAM ANTIBACTERIAL AGENTS

This invention relates to a novel family of β-lactam antibacterials, synthetic methods and intermediates useful in the production of such antibacterials, and the use of such compounds as antibacterial agents. The invention relates more particularly to monocyclic β-lactams bearing on isoxazolyl-amino-sulfonylaminocarbonyl substituent at the 1-position.

The novel family of β-lactam antibacterials of the present invention encompasses compounds of the formula

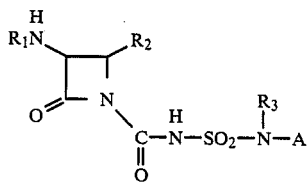

or wherein A is

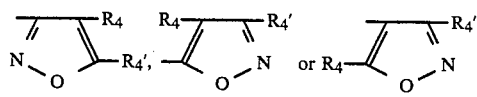

$R_1$ is acyl, $R_2$ is hydrogen, lower alkyl, lower alkoxycarbonyl or aminocarbonyl, $R_3$ is hydrogen, and lower alkyl, and $R_4$ and $R_4'$ are each hydrogen, lower alkyl, which may be substituted, lower alkoxy which may be substituted, aryl, substituted aryl, aryloxy, substituted aryloxy or aralkyl.

Exemplary substituents to be substituted on other radicals, include, cyano, amino, lower alkyl, lower alkoxy, mercapto, lower alkylthio and the like.

The invention is also considered to encompass pharmaceutically acceptable salts of compounds of the formula I. Examples of salts provided by the present invention are salts with bases; for example, alkali metal salts such as the sodium salt and the potassium salt, the ammonium salt, alkaline earth metal salts such as the calcium salt, salts with organic bases such as salts with amines (e.g. salts with N-ethylpiperidine, procaine, dibenzylamine, N,N'-dibenzylethylethylenediamine, alkylamines or dialkylamines) and salts with amino acids (e.g. salts with arginine or lysine).

As used in this specification, the term "lower alkyl" or "alkyl" refers to both straight and branched chain saturated hydrocarbon groups having 1 to 8 and preferably, 1 to 4 carbon atoms, which may or may not be substituted, such as, for example, methyl, ethyl, propyl, isopropyl, tertiary butyl, halomethyl such as chloromethyl or bromomethyl and the like.

As used herein, the term "aralkyl" refers to groups comprising a lower-alkyl residue substituted by one or more aryl or substituted aryl groups, such as, for example, phenylmethyl, phenylethyl, phenylpropyl, phenylisopropyl, phenyl-tertiary butyl, hydroxyphenyl methyl and the like.

As used herein, the term "aryl" or "ar" as in aralkyl, for example, refers to carbocyclic aromatic group, which can be substituted or unsubstituted, such as, for example, phenyl, hydroxyphenyl, tolyl, chlorophenyl and the like.

The term "halo" as used herein represents all four forms thereof, i.e. chloro, bromo, iodo or fluoro unless otherwise specified.

As used herein, the term "lower alkoxy" refers to substituted or unsubstituted alkoxy groups wherein the "alkyl" portion is a lower alkyl group as defined hereinbefore. Exemplary are methoxy, ethoxy, propoxy and the like.

The term "acyl", as used herein, means and includes all organic radicals derived from an organic acid (i.e., a carboxylic acid) by removal of the hydroxyl group. Although the group $R^1$ may be any one of many acyl radicals, certain acyl groups are preferred.

Exemplary acyl groups are those acyl groups which have been used in the past to acylate β-lactam antibiotics including 6-aminopenicillanic acid and derivatives and 7-aminocephalosporanic acid and derivatives; see, for example, Cephalosporins and Penicillins, edited by Flynn, Academic Press (1972), Belgian Pat. No. 866,038 published Oct. 17, 1978, Belgian Pat. No. 867,994, published Dec. 11, 1978, U.S. Pat. No. 4,152,432, issued May 1, 1979, U.S. Pat. No. 3,971,778, issued July 27, 1976, and U.S. Pat. No. 4,172,199, issued Oct. 23, 1979. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula

wherein $R^5$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

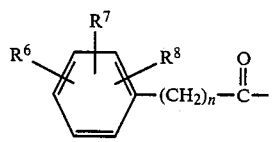

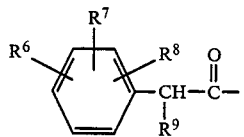

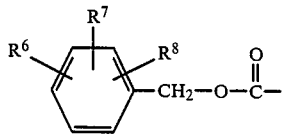

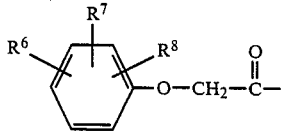

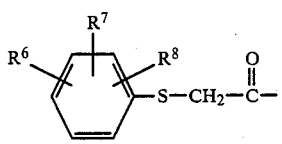

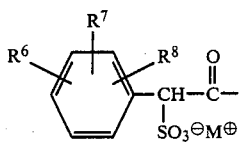

or

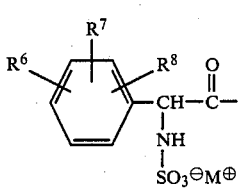

wherein n is 0, 1, 2, or 3; $R^6$, $R^7$, and $R^8$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R^9$ is amino, hydroxyl, a carboxyl salt, protected carboxy, such as benzyloxycarbonyl, formyloxy, a sulfo salt, such as a sodium salt, a potassium salt or an amine salt, a sulfoamino salt, such as a sodium salt, a potassium salt or an amine salt, or azido.

Preferred carbocyclic aromatic acyl groups include those having the formula

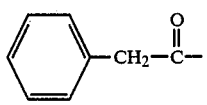

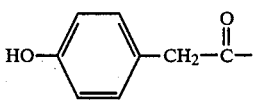

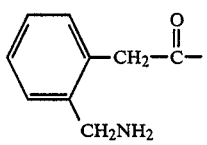

and

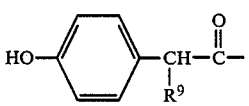

($R^9$ is preferably an amino group, a hydroxy group, or a carboxyl salt or sulfo salt)

Examples of other acyl groups of the formula

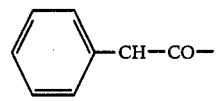

suitable for the purposes of the present invention are α-sulfophenyl-acetyl, α-hydroxysulfonyloxyphenylacetyl, α-sulfamoylphenylacetyl, α-(phenoxycarbonyl)-phenyl-acetyl, α-(p-tolyloxycarbonyl)phenylacetyl, α-formyloxyphenylacetyl, α-carboxyphenylacetyl, α-benzyloxycarbonylphenylacetyl, 2-(N,N-dimethylsulfamoyl)-2-phenylacetyl, 2-bromo-2-thienylacetyl, etc.

(c) Heteroaromatic groups having the formula

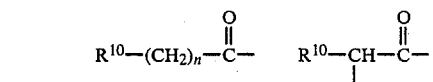
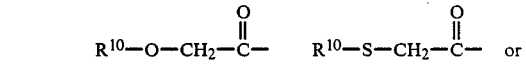
 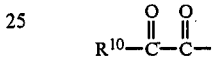

wherein n is 0, 1, 2 or 3; $R^9$ is as defined above; and $R^{10}$ is a substituted or unsubstituted 5-, 6- or 7-membered heterocyclic ring containing 1, 2, 3 or 4 (preferably 1 or 2) nitrogen, oxygen or sulfur atoms. Exemplary heterocyclic rings are thienyl, furyl, pyrrolyl, pyridinyl, pyrazinyl, thiazolyl, pyrimidinyl and tetrazolyl. Exemplary substituents are halogen, hydroxyl, nitro, amino, cyano, trifluoromethyl, alkyl of 1 to 4 carbon atoms, or alkoxy of 1 to 4 carbon atoms.

Preferred heteroaromatic acyl groups include those groups of the above formulas wherein $R^{10}$ is 2-amino-4-thiazolyl, 2-amino-5-halo-4-thiazolyl, 4-aminopyrimidn-2-yl, 2-amino-1,3,4-thiadiazol-5-yl, 2-thienyl or 2-furanyl.

(d) [[(4-Substituted-2,3-dioxo-1-piperazinyl)-carbonyl]amino]arylacetyl groups having the formula

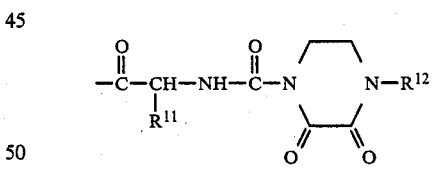

wherein $R^{11}$ is an aromatic group (including carbocyclic aromatics such as those of the formula

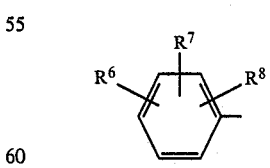

wherein $R^6$, $R^7$, and $R^8$ are as previously defined and heteroaromatics as included within the definition of $R^{10}$); and $R^{12}$ is alkyl, substituted alkyl (wherein the alkyl group is substituted with one or more halogen, cyano, nitro, amino or mercapto groups) e.g. 4-lower alkyl (preferably ethyl or methyl)-2, 3-dioxo-1-piperazinecarbonyl-D-phenylglycyl.

(e) (Substituted oxyimino) arylacetyl groups having the formula

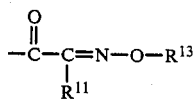

wherein $R^{11}$ is as defined above and $R^{13}$ is hydrogen, lower alkyl and $C_3$–$C_7$ cycloalkyl or substituted lower alkyl (wherein the alkyl group is substituted with 1 or more halogen, cyano, nitro, amino, mercapto, lower alkylthio, aromatic group (as defined by $R^{11}$), carboxyl (including salts thereof), amido, lower alkoxycarbonyl, phenylmethoxycarbonyl, diphenylmethoxycarbonyl, hydroxyalkoxyphosphinyl, dihydroxyphosphinyl, hydroxy (phenylmethoxy) phosphinyl, or diloweralkoxyphosphinyl substituents).

Examples of

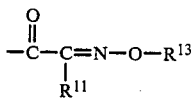

grouping are
2-[(2-chloroacetamidothiazol-4-yl)-2-[(p-nitrobenzyloxycarbonyl]methoxyimino]acetyl
2-(2-chloroacetamidothiazol-4-yl)-2-methoxyiminoacetyl,
2-(2-aminothiazol-4-yl)-2-isopropoxy-iminoacetyl,
2-(2-aminothiazol-4-yl)-2-methoxyiminoacetyl,
2-(2-aminothiazol-4-yl)-2-oxyiminoacetyl,
2-thienyl-2-methoxyiminoacetyl,
2-furyl-2-methoxyiminoacetyl,
2-(4-hydroxyphenyl)-2-methoxyiminoacetyl,
2-phenyl-2-methoxy-iminoacetyl, 2-phenyl-2-hydroxyiminoacetyl,
2-thienyl-2-hydroxyiminoacetyl, 2-thienyl-2-(dichloroacetyloxyimino)acetyl, 2-[4-(γ-D-glutamyloxy)phenyl]-2-oxyiminoacetyl,
2-[4-(3-amino-3-carboxypropoxy)phenyl]-2-oxyiminoacetyl,
2-(5-chloro-2-chloro-acetamidothiazol-4-yl)-2-methoxyiminoacetyl,
2-(5-chloro-2-aminothiazol-4-yl)-2-methoxyiminoacetyl,
2-[γ-(t-butoxy-carbonyl)isopropoxyimino]-2-(2-sulfoaminothiazol-4-yl)-acetyl,
2-[γ-(t-butoxycarbonyl)isopropoxyimino]-2-(2-triphenylmethylamino-thiazol-4-yl)acetyl,
2-(2-chloroacetamidothiazol-4-yl)-2-isopropoxyiminoacetyl,
2-methoxyimino-2-(2-sulfoaminothiazol-4-yl)acetyl,
2-[(2-aminothiazol-4-yl)-2-carboxymethoxyimino]acetyl
2-[2-(2-mesylaminothiazol-4-yl)-2-isopropoxyiminoacetyl,
2-(2-imino-3-mesyl-4-thiazolin-4-yl)-2-isopropoxyiminoacetyl,
2-[(2-Aminothiazol-4-yl)-2-(carboxyisopropoxyimino)acetyl etc.

(f) (Acylamino) arylacetyl groups having the formula

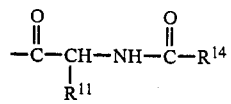

wherein $R^{11}$ is as defined above and $R^{14}$ is

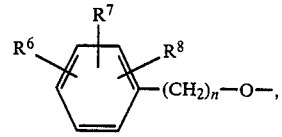

amino alkylamino, (cyanoalkyl) amino, or acylamino.

Preferred (acylamino) arylacetyl groups of the above formula include those groups wherein $R^{14}$ is amino, or acylamino. Also preferred are those groups wherein $R^{11}$ is phenyl or 2-thienyl.

(g) [[[3-Substituted-2-oxo-1-imidazolidinyl]carbonyl]amino]arylacetyl groups having the formula

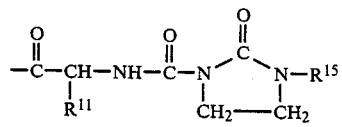

wherein $R^{11}$ is as defined above and $R^{15}$ is hydrogen, alkylsulfonyl, arylmethyleneamino (i.e., —N=CH—$R^{11}$ wherein $R^{11}$ is as defined above),

(wherein $R^{16}$ is hydrogen, alkyl or halogen substituted alkyl), aromatic group (as defined by $R^{11}$ above), alkyl or substituted alkyl (wherein the alkyl group is substituted with one or more halogen, cyano, nitro, amino or mercapto groups).

Preferred [[[3-substituted-2-oxo-1-imidazolidinyl]carbonyl]amino]arylacetyl groups of the above formula include those wherein $R^{11}$ is phenyl or 2-thienyl. Also preferred are those groups wherein $R^{15}$ is hydrogen, methylsulfonyl, phenylmethyleneamino or 2-furylmethyleneamino.

Especially preferred are compounds of the formula

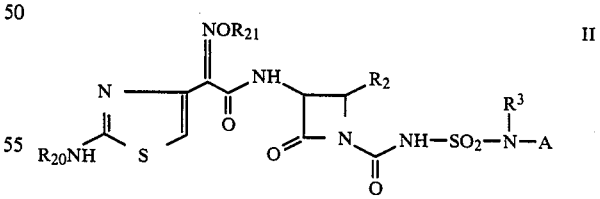

where A is

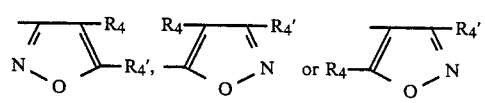

wherein $R_2$, $R_3$, $R_4$, and $R_4'$ are as previously defined, $R_{20}$ is hydrogen or an amino protecting group such as trityl or chloroacetyl, $R_{21}$ is hydrogen, lower alkyl, or a group of the formula

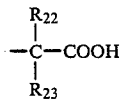

wherein $R_{22}$ and $R_{23}$ are selected from the group consisting of hydrogen and lower alkyl, or $R_{22}$ and $R_{23}$ taken together with the carbon atom to which they are attached form a 3–7 carboxylic ring e.g. cyclopropyl, cyclobutyl or cyclopentyl. Still more preferred are compounds of the formula II in which $R_2$, $R_3$, $R_4$, and $R_4'$ are each hydrogen or methyl, $R_{20}$ is hydrogen, and $R_{21}$ is methyl or a group of the formula

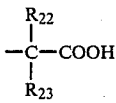

wherein $R_{22}$ and $R_{23}$ are each either hydrogen or methyl.

It will be observed that compounds of formula I have a chiral center at the position 3 carbon atom of the β-lactam ring. In compounds encompassed by the invention, the stereo configuration of the position 3 chiral carbon atoms is the same as that of the position 6 carbon atom in naturally occurring penicillins, such as penicillin G, and of the position 7 carbon atom in naturally occurring cephalosporins, such as cephalosporin C. Pursuant to convention, this stereo configuration of the position 3 carbon atom in compounds of formula I is designated the "S" configuration.

Mixtures of the S and R isomers of Compound I, such as racemic mixtures, are also considered to be within the scope of the invention.

The group $R^2$, which is a substituent of the position 4 carbon atom, may be either cis or trans with respect to the acylamino group attached to the position 3 carbon atom.

β-lactam compounds according to the invention have activity against a broad spectrum of both gram-negative and gram-positive bacteria.

The compounds of this invention can be used as agents to combat bacterial infection (including urinary tract infections and respiratory infections) in mammalian species, such as domesticated animals (e.g., dogs, cats, cows, horses, and the like) and humans.

For combating bacterial infections in mammals a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with the novel family of β-lactams of this invention. Such methods of administration include oral, intravenous, intramuscular and as a suppository.

Compounds of Formula I can be prepared utilizing a known, starting material, having the formula

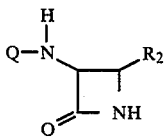

or the formula

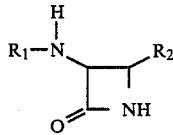

wherein Q is any known amino protecting group, such as, for example, benzyloxycarbonyl (CBZ) or tert-butyloxycarbonyl (t-BOC), and wherein $R^1$ and $R^2$ are the same as hereinbefore described.

Compounds of the formula I above are prepared in one process embodiment in two stages. In the first stage, a compound of the formula IV is reacted with a compound of the formula $$O=C=N-SO_2-X$$

wherein X is a leaving group e.g. a halogen such as chlorine. The first stage is suitably run in a dry inert organic solvent such as acetonitrile, methylene chloride, 1,2-dimethoxyethane, THF, dioxane and the like.

A preferred compound for this purpose is chlorosulphonyl isocyanate. Suitably, this first stage is effected below room temperature, i.e., in the cold, suitably at −70° C., to about 10° C. preferably from about −55° C. to about 0° C.

The second stage occurs by adding to the reaction medium upon completion of the first stage, a compound of the formula

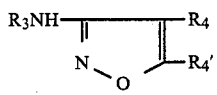

a compound of the formula

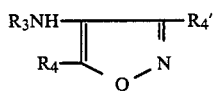

or a compound of the formula

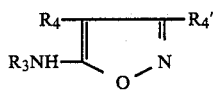

wherein $R_3$, $R_4$ and $R_4'$, are as above, together with a suitable tertiary amine or amines, such as triethylamine and pyridine. The two-stage reaction is conducted under anhydrous conditions, preferrably under an inert gas such as argon.

It should be understood that if it is desired to prepare a compound of the formula I above which contains a functional group such as a hydroxyl group or an amino radical present in the $R_1$ acyl chain which would react under the conditions utilized in the condensation of an isocyanate, such functional groups must be protected, in a manner known in the art, using suitable protecting groups such as t-BOC, CBZ, trityl, or chloroacetyl. Such protecting groups are removed in a subsequent step or steps to give the desired compound of formula I. Alternatively, a compound of the formula III can be used as starting material. That is to say, the compound of the formula III which bears a protecting group is first utilized for the two-stage reaction. The protecting group is then removed giving $R_1$ as hydrogen and the desired acyl group is introduced to obtain the desired compound of the formula I according to procedures well known in the art.

The Examples which follow further illustrate the invention in more detail, but are not intended to limit its extent. In the Examples all temperatures are given in degrees Centigrade, unless otherwise stated.

EXAMPLE 1

(S)-N-[1-[[[[(5-Methyl-3-isoxazolyl)amino]sulfonyl]amino]-carbonyl]-2-oxo-3-azetidinyl]benzeneacetamide A mixture of 204 mg (1 mmol) of (S)-N-(2-oxo-3-azetidinyl)benzeneacetamide and 10 mL of 1,2-dimethoxyethane was stirred and cooled. At 0°–5° C. 0.104 mL of chlorosulfonyl isocyanate was added; within 5 minutes complete solution occurred. The reaction mixture was kept at 0°–5° C. for one hour. Then, with cooling to −10° C., a mixture of 98 mg (1 mmol) of 5-methyl-3-isoxazolamine, 0.415 mL (3 mmol) of triethylamine, and 0.30 mL (3 mmol) of pyridine was added. The cold bath was removed, and stirring continue for two hours. The mixture was then concentrated under reduced pressure, the residue dissolved in methylene chloride, and the solvent evaporated to leave an amorphous residue, which was then dissolved in a mixture of ethyl acetate and water. The mixture was acidified to pH 3; the organic layer was dried ($Na_2SO_4$), treated with charcoal, filtered, and concentrated to a residue of 180 mg. Purification was accomplished by preparative layer chromatography on three 20×20 cm Merck PLC plates (Silica Gel 60 F-254) using 10% MeOH in $CHCl_3$ as the solvent to obtain the title compound: ($Me_2SO$-$d_6$) δ 2.29 (s, 3H, Me), 3.25 (dd, $J_{4\alpha, 4\beta}$=6 Hz, $J_{3, 4\beta}$=3 Hz, 1H, CHCHαHβ), 3.45 (s, 2H, PhCH$_2$), 3.60 (t, $J_{3, 4\alpha}$=$J_{4\alpha, 4\beta}$=6 Hz, 1H, CHCHα Hβ), 4.75 (m, 1H, CHCH$_2$), 6.13 (s, 1H, isoxazole H) 7.27 (s, 5H, Ph), 8.74 (d, J=8 Hz, 1H, NHCH), 8.97 (bs, 1H, NH); 1R (KBr) 3420, 1773, 1650, 1620, 1358, 1310, 1133 cm$^{-1}$.

EXAMPLE 2

S-[1-[[[[(5-Methyl-3-isoxazolyl)amino]sulfonyl]amino]-carbonyl]-2-oxo-3-azetidinyl]carbamic acid phenylmethyl ester A mixture of 2.20 g (0.01 mol) of (S)-(2-oxo-3-azetidinyl)carbamic acid phenylmethyl ester and 40 mL of acetonitrile was stirred and cooled in an ice bath, and 0.90 mL (0.01 mol) of chlorosulfonyl isocyanate was added. After ten minutes, during which time complete solution occurred, a solution of 0.98 g (0.01 mol) of 5-methyl-3-isoxazolamine in 8 mL of acetonitrile was added. After another five minutes, 1.40 mL (0.01 mol) of triethylamine was added. The mixture was stirred for 15 minutes at 0°, and one hour at room temperature. The mixture was concentrated under reduced pressure; methylene chloride was added, and concentration under reduced pressure was repeated. The residue was dissolved in a mixture of ethyl acetate and ice-water, and adjusted to pH 3 with 0.5N HCl. The organic phase was washed with water, dried ($Na_2SO_4$), treated with charcoal, filtered and concentrated under reduced pressure. Methylene chloride was added, and the solution again concentrated under reduced pressure. The residue was crystallized from ethanol to yield 2.30 g of the title compound, melting at 140°–142° C.: NMR ($Me_2SO$-$d_6$) δ 2.34 (s, 3H, Me), 3.59 (m, 1H, CHCHα CHβ), 3.86 (t, $J_{3, 4\alpha}$=$J_{4\alpha, \beta}$=6 Hz, 1H, CHCHα CHβ), 4.84 (m, 1H, CHCH$_2$), 5.05 (s, 2H, Ph CH$_2$), 6.16 (s, 1H, isoxazole H), 7.37 (s, 5H, Ph), 8.02 (d, J=8 Hz, NHCH); 1R (KBr) 3400, 3170, 1800, 1725, 1700, 1335, 1185 cm$^{-1}$; mass spectrum (FAB) m/z 414 (M+H)$^+$.

EXAMPLE 3

(S,Z)-2-Amino-α-(methoxyimino)-N-[1-[[[[(5-methyl-3-isoxazolyl)amino]sulfonyl]amino]carbonyl]-2-oxo-3-azetidinyl]thiazole-4-acetamide Sodium Salt A solution of 716 mg (1.4 mmol) of (S,Z)-α-methoxyimino-N-(2-oxo-3-azetidinyl)-2-[(triphenylmethyl)amino]thiazole-4-acetamide (prepared according to European Pat. No. 62 876, example 4B) in 10 mL of 1,2-dimethoxyethane was prepared at 40° C. and quickly cooled in ice. At 0° C., 0.15 mL (1.68 mmol) of chlorosulfonyl isocyanate was added. The mixture was stirred at 0° for one hour, and then cooled to −10° C. A mixture of 137 mg (1.4 mmol) of 5-methyl-3-isoxazolamine, 0.62 mL of triethylamine, and 0.36 mL of pyridine was then added. The cold bath was removed, and stirring continued for 2 hours. The mixture was concentrated under reduced pressure, and $CH_2Cl_2$ was added to the residue. After further evaporation under reduced pressure an amorphous solid was obtained. This intermediate was purified by preparative layer chromatography on seven 20×20 cm Merck PLC plates (Silica Gel 60F-254), using 10% MeOH in $CHCl_3$ as the solvent to obtain 500 mg of solid. This material was stirred with 20 mL of 70% formic acid for 4 hours, the mixture filtered, and the filtrate evaporated to dryness under reduced pressure. A 200 mg portion of the residue so obtained was suspended in a mixture of 12 mL of $H_2O$ and 12 mL of EtOAc. With cooling in ice, 0.1N NaOH was added to adjust the pH to 7.5. The aqueous phase was partly evaporated under reduced pressure and finally freeze-dried to yield the title compound.

EXAMPLE 4

[3S-trans;(Z)]-α-(Methoxyimino)-N-[4-methyl-2-oxo-3-azetidinyl]-2-[(triphenylmethyl)amino]thiazole-4-acetamide A mixture of 936 mg (0.004 mol) of (3S-trans)-(4-methyl-2-oxo-3-azetidinyl)carbamic acid phenylmethyl ester, 50 mL of methanol, and 270 mg of 10% palladium on carbon catalyst was hydrogenated (5 minutes) on a Parr apparatus at an initial gauge pressure of 50 psi. After filtration of the catalyst, the solution was concentrated to dryness under reduced pressure. The residual [3S-trans]-3-amino-4-methyl-2-azetidinone was dissolved in 2 mL of DMF and added to a stirred mixture of 1.7 g (0.004 mol) (Z)-α-methoxyimino-2-[(triphenylmethyl)amino]thiazole-4-acetic acid, 20 mL of DMF, 540 mg (0.004 mol) of 1-hydroxybenzotriazole, and 824 mg (0.004 mol) N,N'-dicyclohexylcarbodiimide. The mixture was stirred 4 hours, diluted with 200 mL of water, and adjusted to pH 7.5 with aqueous $NaHCO_3$. The mixture was extracted with three 300 mL portions of ethyl acetate, and the combined extracts washed with water and brine, dried ($Na_2SO_4$), and decolorized with charcoal. The amorphous solid obtained by evaporation of the solvent was purified by HPLC on a Waters Prep 500 using 4:1 ethyl acetate-hexane, to obtain 1.2 g of product.

[3S-trans;(Z)]-2-Amino-α-(methoxyimino)-N-[4-methyl-1-[[[[(5-methyl-3-isoxazolyl)amino]sulfonyl]amino]carbonyl]-2-oxo-3-azetidinyl]thiazole-4-acetamide Sodium Salt A mixture of 368 mg (0.7 mmol) of [3S-trans;(Z)]-α-(methoxyimino)-N-[4-methyl-2-oxo-3-azetidinyl]-2-[(triphenylmethyl)amino]thiazole-4-acetamide and 5 mL of 1,2-dimethoxyethane was cooled to 0° C. and treated with 0.074 mL (0.84 mmol) of chlorosulfonyl isocyanate. After one hour at 0°, the mixture was cooled to −15°, and a solution of 68.6 mg (0.7 mmol) of 5-methyl-3-isoxazolamine, 0.31 mL of triethylamine, and 0.18 mL of pyridine in 2 mL of 1,2-dimethoxyethane was added. The cold bath was removed, and the mixture stirred for 2 hours, before concentrating under reduced pressure. Methylene chloride was added to the residue, and evaporation was repeated. The residue was purified by preparative layer chromatography on eight 20×20 cm Merck PLC plates (Silica Gel 60F-254), using 20% methanol in chloroform as the solvent. The intermediate (200 mg) thus obtained was stirred for 4 hours with 7 mL of 70% formic acid. The mixture was concentrated under reduced pressure, methylene chloride was added, and evaporation repeated. With cooling in ice, the residue was dissolved in 10 mL of ethyl acetate and 10 mL of water, and the mixture adjusted to pH 7.5 with 0.1N NaOH. The aqueous phase was washed repeatedly with ethyl acetate, concentrated under reduced pressure to eliminate volatile solvent, and freeze dried to obtain [3S-trans;(Z)]-2-Amino-α-(methoxyimino)-N-[4-methyl-1-[[[[(5-methyl-3-isoxazolyl)amino]sulfonyl]amino]carbonyl]-2-oxo-3-azetidinyl]-thiazole-4-acetamide sodium salt as a white solid: NMR (Me$_2$SO-d$_6$) δ 1.38 (d, J=7 Hz, 3H, CHMe), 2.30 (s, 3H, isoxazole Me), 3.75 (m, 1H, CHMe), 3.84 (s, 3H, NOMe), 4.38 (m, 1H, CHNH), 6.12 (s, 1H, isoxazole H), 6.72 (s, 1H, thiazole H), 7.23 (s, 2H, NH$_2$), 8.51 (s, 1H, NH), 9.19 (d, J=8 Hz, 1H, NHCH); IR (KBr) 3430, 1780, 1620, 1368, 1135 cm$^{-1}$.

EXAMPLE 5

(S,Z)-α-[[2-(1,1-dimethylethoxy)-1,1-dimethyl-2-oxoethoxy]imino]-N-(2-oxo-3-azetidinyl)-2-[(triphenylmethyl)amino]-4-thiazoleacetamide A mixture of 2.20 g (0.01 mmol) of (S)-(2-oxo-3-azetidinyl) carbamic acid phenylmethyl ester, 125 mL of methanol, and 0.68 g of 10% palladium on carbon catalyst was hydrogenated (5 minutes) on a parr apparatus at an initial gauge pressure of 50 psi. After filtration of the catalyst, the solution was concentrated to dryness under reduced pressure. The residual (S)-3-amino-2-azetidinone was dissolved in 10 mL of DMF and added to a mixture of 5.71 g (0.01 mol) of (Z)-α-[[2-(1,1-dimethylethoxy)-1,1-dimethyl-2-oxoethoxy]imino]-2-[(triphenylmethyl)amino]-4-thiazole acetic acid, 40 mL of DMF, 2.06 g (0.01 mol) of N,N'-dicyclohexylcarbodiimide and 1.35 g (0.01 mol) of 1-hydroxybenzotriazole. The mixture was stirred for 4 hours, diluted with 500 mL of water, and adjusted to pH 7.5 with aqueous NaHCO$_3$. The mixture was extracted with four 300 mL portions of ethyl acetate. The combined extracts were washed with water and brine, dried (Na$_2$SO$_4$), decolorized with charcoal, and concentrated to dryness. After purification by HPLC on a Waters Prep 500, using 4:1 ethyl acetate-hexane, 3.8 g of (S,Z)-α-[[2-(1,1-dimethylethoxy)-1,1-dimethyl-2-oxoethoxy]imino]-N-(2-oxo-3-azetidinyl)-2-[(triphenylmethyl)amino]-4-thiazoleacetamide was obtained.

(S,Z)-2-[[[1-(2-Amino-4-thiazolyl)-2-[1-[[[[(5-methyl-3-isoxazolyl)amino]sulfonyl]amino]carbonyl]-2-oxo-3-azetidinyl]amino-2-oxoethylidene]imino]oxy]-2-methylpropanoic acid dipotassium salt A mixture of 447 mg (0.7 mmol) of (S,Z)-α-[[2-(1,1-dimethylethoxy)-1,1-dimethyl-2-oxoethoxy]imino]-N-(2-oxo-3-azetidinyl)-2-[(triphenylmethyl)amino]-4-thiazoleace tamide and 5 mL of 1,2-dimethoxyethane was cooled to 0° C. and treated with 0.074 mL (0.84 mmol) of chlorosulfonyl isocyanate. After one hour at 0° C., the mixture was further cooled to −15° C. and a solution of 68.6 mg (0.7 mmol) of 5-methyl-3-isoxazolamine, 0.31 mL of triethylamine, and 0.18 mL of dry pyridine in 2 mL of 1,2-dimethoxyethane was added. The cold bath was removed and the mixture stirred for two hours before concentrating under reduced pressure. Methylene chloride was added, and the evaporation repeated. The residue was purified by preparative layer chromatography on twelve 20×20 cm Merck PLC plates (Silica Gel 60F-254) using 20% methanol in chloroform as the solvent. The 250 mg of intermediate thus obtained was suspended in 1 mL of anisole, and cooled at −5° C.; 5 mL of trifluoroacetic acid was added, maintaining the temperature at −5° to 0° C. The resulting solution was allowed to stand at 0° for 24 hours. The mixture was concentrated to dryness under reduced pressure, with continued cooling at 0°. Methylene chloride was added to the residue, and the evaporation repeated. The residue was then triturated with 20 mL of petroleum ether to obtain 200 mg of a solid. This was added to a cold mixture of 10 mL of ethyl acetate, 0.9 mL of N KHCO$_3$, and 5 mL of water, obtaining a pH of 7.5. The aqueous phase was mixed with a fresh 15 mL portion of ethyl acetate, and by addition of 0.9 mL of N HCl followed by 0.3 mL of N KHCO$_3$ adjusted to pH 4.5. The organic phase was removed, and 10 mL of fresh ethyl acetate was added to the aqueous phase. The pH was adjusted to 3 by addition of 0.35 mL of NHCl. The aqueous phase was removed, and 10 mL of water added to the organic phase. The pH was adjusted to 7.5 by addition of N KOH. The aqueous phase was then concentrated under reduced pressure to eliminate volatile solvent, and freeze dried to yield 56 mg of (S,Z)-2-[[[1-(2-Amino-4-thiazolyl)-2-[1-[[[[(5-methyl-3-isoxazolyl)amino]sulfonyl]amino]carbonyl]-2-oxo-3-azetidinyl]amino-2-oxoethylidene]imino]oxy]-2-methylpropanoic acid dipotassium salt:
NMR (D$_2$O) δ1.47, 1.49 (2s, 6H, Me$_2$), 2.36 (s, 3H, isoxazole Me), 3.73 (dd, J$_{4\alpha,4\beta}$=6 Hz and J$_{3,4\beta}$=3.5 Hz, 1H, CHCHα Hβ), 3.98 (t, J$_{4\alpha,4\beta}$=J$_{3,4\alpha}$=6 Hz, 1H, CHCHα Hβ), 5.03 (dd, J$_{3,4\alpha}$=6 Hz and J$_{3,4\beta}$=3.5 Hz, 1H, CHCHα Hβ), 6.16 (s, 1H, isoxazole H), 6.96 (s, 1H, thiazole H); IR (KBr) 3400, 1780, 1682, 1350, 1130 cm$^{-1}$.

EXAMPLE 6

As in Example 4, there can be additionally prepared (S)-N-[1-[[[[(5-Methyl-3-isoxazolyl)amino]sulfonyl]amino]carbonyl]-2-oxo-3-azetidinyl]thiophene-2-acetamide.

EXAMPLE 7

As in Example 4 there can be additionally prepared (S)-N-[1-[[[[(5-Methyl-3-isoxazolyl)amino]sulfonyl- ]amino]carbonyl]-2-oxo-3-azetidinyl]-tetrazole-1-acetamide.

EXAMPLE 8

As in Example 4, there can be additionally prepared (S)-3-(2,6-Dichlorophenyl)-5-methyl-N-[1-[[[[(5-methyl-3-isoxazolyl)amino]sulfonyl]-amino]carbonyl]-2-oxo-3-azetidinyl]isoxazole-4-carboxamide.

EXAMPLE 9

As in Example 4, there can be additionally prepared (S)-2-aminomethyl-N-[1-[[[[(5-methyl-3-isoxazolyl)amino]sulfonyl]amino]carbonyl]-2-oxo-3-azetidinyl]-benzeneacetamide.

EXAMPLE 10

As in Example 4, there can be additionally prepared (S)-α-cyano-N-[1-[[[[(5-methyl-3-isoxazolyl)amino]sulfonyl]amino]carbonyl]-2-oxo-3-azetidinyl]acetamide.

EXAMPLE 11

As in Example 4, there can be additionally prepared (S)-α-[(cyanomethyl)-thio]-N-[1-[[[[(5-methyl-3-isoxazolyl)amino]sulfonyl]amino]carbonyl]-2-oxo-3-azetidinyl]acetamide.

EXAMPLE 12

As in Example 4, there can be additionally prepared [3S-(3β),(R*)]-α-[[(2,3-dioxo-4-ethyl-1-piperazinyl)carbonyl]amino]-N-[1-[[[[(5-methyl-3-isoxazolyl)amino]-sulfonyl]amino]carbonyl]-2-oxo-3-azetidinyl]propanamide.

EXAMPLE 13

As in Example 4, there can be additionally prepared [3S-(3β),(R*)]-α-[[(3,4-dioxo-4-ethyl-1-piperazinyl)carbonyl]amino]-N-[1-[[[[(5-methyl-3-isoxazolyl)amino]-sulfonyl]amino]carbonyl]-2-oxo-3-azetidinyl]benzeneacetamide.

EXAMPLE 14

As in Example 4, there can be additionally prepared [3S-(3β),(R*)]-α-[[(2,3-dioxo-4-ethyl-1-piperazinyl)carbonyl]amino]-4-methoxy-N-[1-[[[[(5-methyl-3-isoxazolyl)amino]sulfonyl]amino]carbonyl]-2-oxo-3-azetidinyl]benzeneacetamide.

EXAMPLE 15

As in Example 4, there can be additionally prepared [3S-(3β),(S*)]-α-[[(2,3-Dioxo-4-ethyl-1-piperazinyl)carbonyl]amino]-N-[1-[[[[(5-methyl-3-isoxazolyl)amino]-sulfonyl]amino]carbonyl]-2-oxo-3-azetidinyl]thiophene-2-acetamide.

EXAMPLE 16

As in Example 4, there can be additionally prepared [3S-(3β),(S*)]-α-[[(2,3-Dioxo-4-octyl-1-piperazinyl)carbonyl]-amino]-N-[1-[[[[(5-methyl-3-isoxazolyl)amino]-sulfonyl]-amino]carbonyl]-2-oxo-3-azetidinyl]thiophene-2-acetamide.

EXAMPLE 17

As in Example 4, there can be additionally prepared [3S-(3β),(R*)]-α-[[(2,3-Dioxo-4-octyl-1-piperazinyl)-carbonyl]-amino]-N-[1-[[[[(5-methyl-3-isoxazolyl)amino]sulfonyl]-amino]carbonyl]-2-oxo-3-azetidinyl]-benzeneacetamide.

EXAMPLE 18

As in Example 4, there can be additionally prepared (S)-2-amino-N-[1-[[[[(5-methyl-3-isoxazolyl)amino]-sulfonyl]amino]carbonyl]-2-oxo-3-azetidinyl]-thiazole-4-acetamide.

EXAMPLE 19

As in Example 4, there can be additionally prepared (S,Z)-α-Methoxyimino-N-[1-[[[[(5-methyl-3-isoxazolyl)amino]sulfonyl]amino]carbonyl]-2-oxo-3-azetidinyl]-benzeneacetamide.

EXAMPLE 20

As in Example 4, there can be additionally prepared (S,Z)-α-Methoxyimino-N-[1-[[[[(5-methyl-3-isoxazolyl)amino]sulfonyl]amino]carbonyl]-2-oxo-3-azetidinyl]-thiophene-2-acetamide.

EXAMPLE 21

As in Example 4 there can be additionally prepared [3S-(3β),(S*)]-α-[[[3-[2-(Furylmethylene)amino]-2-oxo-1-imidazolidinyl]carbonyl]amino]-N-[1-[[[[(5-methyl-3-isoxazolyl)amino]sulfonyl]amino]carbonyl]-2-oxo-3-azetidinyl]thiophene-2-acetamide.

EXAMPLE 22

As in Example 1 there can be additionally prepared [3S-(3β),(R*)]-N-[1-[[[[(5-methyl-3-isoxazolyl)amino]sulfonyl]amino]carbonyl]-2-oxo-3-azetidinyl]-α-[[[3-[2-(thienylmethylene)amino]-2-oxo-1-imidazolidinyl]carbonyl]amino]benzeneacetamide.

EXAMPLE 23

As in Example 4 there can be additionally prepared [3S-(3β),(R*)]-α-amino-N-[1-[[[[(5-methyl-3-isoxazolyl)amino]sulfonyl]amino]carbonyl]-2-oxo-3-azetidinyl]-benzeneacetamide.

EXAMPLE 24

As in Example 4 there can be additionally prepared (3S)-α-[[[1-[[[[(5-Methyl-3-isoxazolyl)amino]sulfonyl]amino]carbonyl]-2-oxo-3-azetidinyl]amino]carbonyl]-benzeneacetic acid.

EXAMPLE 25

As in Example 4 there can be additionally prepared (S,Z)-5-Amino-α-ethoxyimino-N-[1-[[[[(5-methyl-3-isoxazolyl)amino]sulfonyl]amino]carbonyl]-2-oxo-3-azetidinyl]-1,2,4-thiadiazole-3-acetamide.

EXAMPLE 26

As in Example 4 there can be additionally prepared (S,Z)-[[[1-(2-Amino-4-thiazolyl)-2-[1-[[[[(5-methyl-3-isoxazolyl)amino]sulfonyl]amino]carbonyl]-2-oxo-3-azetidinyl]amino-2-oxoethylidene]imino]oxy]acetic acid.

EXAMPLE 27

As in Example 4 there can be additionally prepared (S,Z-2-[[[1-(2-Amino-4-thiazolyl)-2-[1-[[[[(3-methyl-5-isoxazolyl)amino]sulfonyl]amino]carbonyl]-2-oxo-3-azetidinyl]amino-2-oxoethylidene]imino]oxy]-2-methyl-propanoic acid.

EXAMPLE 28

As in Example 4 there can be additionally prepared (S,Z)-2-Amino-α-(methoxyimino)-N-[1-[[[[(3-methyl-5- isoxazolyl)amino]sulfonyl]amino]carbonyl]-2-oxo-3-azetidinyl]thiazole-4-acetamide.

EXAMPLE 29

As in Example 4 there can be additionally prepared (S,Z)-[[[1-(2-Amino-4-thiazolyl)-2-[1-[[[[(3-methyl-5-isoxazolyl)amino]sulfonyl]amino]carbonyl]-2-oxo-3-azetidinyl]amino-2-oxoethylidene]imino]oxy]acetic acid.

EXAMPLE 30

As in Example 4 there can be additionally prepared (S,Z)-2-Amino-N-[1-[[[[(3,4-dimethyl-5-isoxazolyl)amino]sulfonyl]amino]carbonyl]-2-oxo-3-azetidinyl]-α-(methoxyimino)thiazole-4-acetamide.

EXAMPLE 31

As in Example 4 there can be additionally prepared (S,Z)-2-[[[1-(2-Amino-4-thiazolyl)-2-[1-[[[[(3,4-dimethyl-5-isoxazolyl)amino]sulfonyl]amino]carbonyl]-2-oxo-3-azetidinyl]amino-2-oxoethylidene]imino]oxy]-2-methylpropanoic acid.

EXAMPLE 32

As in Example 4 there can be additionally prepared (S,Z)-[[[1-(2-Amino-4-thiazolyl)-2-[1-[[[[(3,4-dimethyl-5-isoxazolyl)amino]sulfonyl]amino]carbonyl]-2-oxo-3-azetidinyl]amino-2-oxoethylidene]imino]oxy]acetic acid.

EXAMPLE 33

As in Example 4 there can be additionally prepared (S,Z)-2-Amino-N-[1-[[[[(3,5-dimethyl-4-isoxazolyl)amino]sulfonyl]amino]carbonyl]-2-oxo-3-azetidinyl]-α-(methoxyimino)thiazole-4-acetamide.

EXAMPLE 34

As in Example 4 there can be additionally prepared (S,Z)-2-[[[1-(2-Amino-4-thiazolyl)-2-[1-[[[[(3,5-dimethyl-4-isoxazolyl)amino]sulfonyl]amino]carbonyl]-2-oxo-3-azetidinyl]amino-2-oxoethylidene]imino]oxy]-2-methylpropanoic acid.

EXAMPLE 35

As in Example 4 there can be additionally prepared (S,Z)-[[[1-(2-Amino-4-thiazolyl)-2-[2-[[[[(3,5-dimethyl-4-isoxazolyl)amino]sulfonyl]amino]carbonyl]-2-oxo-3-azetidinyl]amino-2-oxoethylidene]imino]oxy]acetic acid.

EXAMPLE 36

As in Example 4 there can be additionally prepared [3S-(3β),(R*)]-α-Hydroxy-N-[1-[[[[(5-methyl-3-isoxazolyl)amino]sulfonyl]amino]carbonyl]-2-oxo-3-azetidinyl]benzeneacetamide.

EXAMPLE 37

As in Example 4 there can be additionally prepared [S-trans; (Z)]-2-[[[1-(2-Amino-4-thiazolyl)-2-[4-methyl-1-[[[[(5-methyl-3-isoxazolyl)amino]sulfonyl]amino]carbonyl]-2-oxo-3-azetidinyl]amino-2-oxoethylidene]imino]oxy]-2-methylpropanoic acid.

EXAMPLE 38

As in Example 4 there can be additionally prepared [S-trans; (Z)]-[[[1-(2-Amino-4-thiazolyl)-2-[4-methyl-1-[[[[(5-methyl-3-isoxazolyl)amino]sulfonyl]amino]carbonyl]-2-oxo-3-azetidinyl]amino-2-oxoethylidene]imino]oxy]acetic acid.

EXAMPLE 39

As in Example 4 there can be additionally prepared [3S-cis; (Z)]-2-Amino-N-[4-[[[(aminocarbonyl)]oxy]methyl]-1-[[[[(5-methyl-3-isoxazolyl)amino]sulfonyl]amino]carbonyl]-2-oxo-3-azetidinyl]-α-(methoxyimino)thiazole-4-acetamide.

EXAMPLE 40

As in Example 4 there can be additionally prepared (cis-rac)-3-[[[2-amino-α-(methoximino)-4-thiazolyl]acetyl]amino]-1-[[[[(5-methyl-3-isoxazolyl)amino]sulfonyl]amino]carbonyl]-4-oxoazetidine-2-carboxylic Acid Ethyl Ester.

EXAMPLE 41

As in Example 4 there can be additionally prepared (S,Z)-2-Amino-N-[1-[[[[(4-methoxy-5-methyl-3-isoxazolyl)amino]sulfonyl]amino]carbonyl]-2-oxo-3-azetidinyl]-α-(methoxyimino)thiazole-4-acetamide.

EXAMPLE 42

As in Example 4 there can be additionally prepared (S,Z)-2-Amino-α-(methoxyimino)-N-[1-[[[[(5-phenyl-3-isoxazolyl)amino]sulfonyl]amino]carbonyl]-2-oxo-3-azetidinyl]thiazole-4-acetamide.

EXAMPLE 43

As in Example 4 there can be additionally prepared (S,Z)-2-Amino-N-[1-[[[[(3,4-dimethyl-5-isoxazolyl)amino]sulfonyl]amino]carbonyl]-2-oxo-3-azetidinyl]-α-[(1-methylethoxy)imino]thiazole-4-acetamide.

EXAMPLE 44

As in Example 4 there can be additionally prepared (S,Z)-2-Amino-α-(ethoxyimino)-N-[1-[[[[5-methyl-3-isoxazolyl)amino]sulfonyl]amino]carbonyl]-2-oxo-3-azetidinyl]thiazole-4-acetamide.

EXAMPLE 45

As in Example 4 there can be additionally prepared (S,Z)-2-Amino-α-(methoxyimino)-N-[1-[[[[methyl(5-methyl-3-isoxazolyl)amino]sulfonyl]amino]carbonyl]-2-oxo-3-azetidinyl]thiazole-4-acetamide.

EXAMPLE 46

As in Example 4 there can be additionally prepared (S,Z)-2-Amino-N-[1-[[[[(5-methyl-3-isoxazolyl)amino]sulfonyl]amino]carbonyl]-2-oxo-3-azetidinyl]-α-[(2,2,2-trifluoroethoxy)imino]thiazole-4-acetamide.

EXAMPLE 47

As in Example 4 there can be additionally prepared [3S-(3β),(R*)]-α-Hydroxy-N-[1-[[[[(5-methyl-3-isoxazolyl)amino]sulfonyl]amino]carbonyl]-2-oxo-3-azetidinyl]benzeneacetamide.

EXAMPLE 48

As in Example 4 there can be additionally prepared (S,Z)-5-Amino-α-ethoxyimino-N-[1-[[[[(5-methyl-3-isoxazolyl)amino]carbonyl]-2-oxo-3-azetidinyl]-1,2,4-thiadiazole-3-acetamide.

EXAMPLE 49

(S)-1-[[[[[(5-Methyl-3-isoxazolyl)amino]sulfonyl]amino]carbonyl]-2-oxo-3-azetidinyl]carbamic acid 1,1-dimethylethyl ester A mixture of 2.60 g (0.014 mol) of (S)-(2-oxo-3-azetidinyl)carbamic acid 1,1-dimethylethyl ester (prepared by the method of D. M. Floyd, et al., J. Org. Chem. 1982, 47, 5160), 80 mL of acetonitrile, and 20 mL of methylene chloride was cooled at $-35°$ to $-45°$ C., and a solution of 2.38 g (0.0168 mol) of chlorosulfonyl isocyanate in 15 mL of methylene chloride was added over a period of 15 minutes. The mixture was stirred for 10 minutes at $-30°$ C. A solution of 1.37 g (0.014 mol) of 5-methyl-3-isoxazolamine, 6.2 mL of triethylamine and 3.6 mL of pyridine in 15 mL of acetonitrile was then added, and stirring was continued for 2 hours at 0° C. The mixture was then concentrated under reduced pressure. Methylene chloride was added, and again the mixture was concentrated under reduced pressure. The residue was dissolved in a mixture of water and ethyl acetate, and NHCl was added, adjusting to pH3. The organic phase was washed with brine, dried ($Na_2SO_4$), treated with charcoal, filtered, and concentrated under reduced pressure to leave 3.2 g of amorphous product: NMR ($Me_2SO-d_6$) $\delta 1.37$ (s, 9H, t-Bu), 2.28 (s, 3H, Me), 3.32 (m, partially obscured by water peak, 1H, CHCH$\alpha$ H$\beta$), 3.55(t, $J_{3,4\alpha}=J_{4\alpha,4\beta}=6$ Hz, 1H, CHCH$\alpha$ H$\beta$), 4.48 (m, 1H, CHCH$\alpha$ H$\beta$), 6.11 (s, 1H, isoxazole H), 7.42 (d, J=9 Hz, 1H, NHCH); IR (KBr) 3370, 1777, 1718, 1622, 1513, 1310, 1150, 1132 $cm^{-1}$.

EXAMPLE 50

(S)-3-Amino-N-[[(5-methyl-3-isoxazolyl)amino]sulfonyl]-2-oxo-1-azetidinecarboxamide trifluoroacetic acid salt A mixture of 7.5 mL of trifluoroacetic acid and 30 mL of anisole was cooled at 0° C., and 1.17 g (3 mmol) of (S)-1-[[[[[(5-methyl-3-isoxazolyl)amino]sulfonyl]amino]carbonyl]-2-oxo-3-azetidinyl]carbamic acid 1,1-dimethylethyl ester was added. The resulting solution was kept at room temperature for 2 hours, before concentrating under reduced pressure. The residue was triturated thoroughly with ether to obtain solid product: NMR ($Me_2SO-d_6$) $\delta 2.30$ (s, 3H, Me), 3.34 (m, 1H, CHCH$\alpha$ H$\beta$), 3.65(m, 1H, CHCH$\alpha$ H$\beta$), 4.42 (m, 1H, CHCH$\alpha$ H$\beta$), 6.15 (s, 1H, isoxazole H), 8.63 (bs, 3H, $NH_3$), 9.21 (bs, 1H, NH), spectrum also shows traces of amisole and ether; IR(KBr) 3420, 3148, 1790, 1730, 1678, 1621, 1509, 1357, 1309, 1134 $cm^{-1}$.

EXAMPLE 51

(S)-N-[1-[[[[(5-Methyl-3-isoxazolyl)amino]sulfonyl]amino]carbonyl]-2-oxo-3-azetidinyl]benzeneacetamide sodium salt by acylation of (S)-3-amino-N-[[(5-methyl-3-isoxazolyl)amino]sulfonyl]-2-oxo-1-azetidinecarboxamide A mixture of 101 mg (0.25 mmol) of (S)-3-amino-N-[[(5-methyl-3-isoxazolyl)amino]sulfonyl]-2-oxo-1-azetidinecarboxamide trifluoroacetic acid salt, 0.5 mL of DMF, and 56 mg (0.55 mmol) of triethylamine was cooled to $-8°$, and a solution of 38.7 mL (0.25 mmol) of phenylacetyl chloride in 1 mL of ethanol-free chloroform was added. After 15 minutes the cold bath was removed and stirring continued for 3 hours at room temperature. The mixture was concentrated under reduced pressure; methylene chloride was added, and evaporation under reduced pressure was repeated. The residue was dissolved in a mixture of ethyl acetate and water, and 0.1N HCl was added to pH3. The organic phase was separated, and the aqueous portion extracted again with ethyl acetate. The organic extracts were combined, washed with brine, dried ($Na_2SO_4$) and concentrated to dryness under reduced pressure. The residue was triturated twice using 15 mL portions of petroleum ether, and then redissolved in methylene chloride. The solvent was evaporated under reduced pressure to leave 90 mg of amorphous solid. This solid was dissolved in ethyl acetate and cooled in ice. Water was added, and the pH was carefully adjusted to 7.5 with 0.1N NaOH. The aqueous phase, after evaporation of solvent, was freeze-dried to yield 70 mg of (S)-N-[1-[[[[(5-methyl-3-isoxazolyl)amino]sulfonyl]amino]carbonyl]-2-oxo-3-azetidinyl]benzeneacetamide sodium salt which was identical in its spectral characteristics to the product prepared in Example 1.

EXAMPLE 52

(S)-1-[[[[[(3-Methyl-5-isoxazolyl)amino]sulfonyl]amino]carbonyl]2-oxo-3-azetidinyl]carbamic acid 1,1-dimethylethylester A mixture of 520 mg (2.80 mmol) of (S)-(2-oxo-3-azetidinyl)carbamic acid 1,1-dimethylethyl ester and 20 mL of 1,2-dimethoxyethane was stirred and cooled to $-30°$ C., and 0.30 ml (3.45 mmol) of chlorosulfonyl isocyanate was added. The mixture was stirred for 10 minutes at $-20°$ C. to obtain a clear solution. Then, at a reaction temperature of $-30°$ C., a cold solution of 255 mg of 3-methyl-5-isoxazolamine, 1.24 mL of triethylamine, and 0.72 mL of pyridine was added during a period of 10 minutes. The mixture was stirred at 0° C. for two hours and concentrated to dryness under reduced pressure. Methylene chloride was added and the evaporation under reduced pressure was repeated. The residue was purified by preparative-layer chromatography on eight 20×20 cm Merck PLC plates (Silica Gel 60F-254) using 1:3 methanol-chloroform as the solvent to obtain 300 mg of product as a white solid: NMR ($Me_2SO-d_6$) 1.38(s, 9H, t-Bu) 2.17 (s, 3H, Me), 3.40-3.90 (m, 2H, $CHCH_2$), 4.70 (m, 1H, $CHCH_2$), 5.80 (s, 1H, isoazole H), 7.56 (d, J=9 Hz, 1H, NHCH) 8.72 (bs, 1H, NH).

EXAMPLE 53

(S)-3-Amino-N-[[3-methyl-5-isoxazolyl)amino]sulfonyl]-2-oxo-1-azetidinecarboxamide trifluoroacetic acid salt A solution of (S)-1-[[[[[(3-methyl-5-isoxazolyl)amino]sulfonyl]amino]carbonyl]-2-oxo-3-azetidinyl]-carbamic acid 1,1-dimethylethyl ester in a 1:4 mixture by volume of trifluoroacetic acid and anisole was prepared at 0° C. and kept at room temperature for 3 hours. The mixture was then concentrated under reduced pressure, and methylene chloride was twice added to the residue, the evaporations under reduced pressure being repeated each time. The residue thus obtained was triturated with acetonitrile to obtain the above product as a solid.

EXAMPLE 54

(S,Z)-2-[(Chloroacetyl)amino]-α-(methoxyimino)-N-[1-[[[[(3-methyl-5-isoxazolyl)amino]sulfonyl]amino]carbonyl]-2-oxo-3-azetidinyl]thiazole-4-acetamide A solution of 100 mg (0.25 mmol) of (S)-3-amino-N-[[(3-methyl-5-isoxazolyl)amino]sulfonyl]-2-oxo-1-azetidinecarboxamide trifluoroacetic acid salt in 0.5 mL of DMF was cooled to −10° and treated with 121 mg (1.2 mmol) of triethylamine. A solution of 83 mg (0.25 mmol) of (Z)-2-[(chloroacetyl)amino]thiazole-4-acetyl chloride hydrochloride in 2.5 mL of ethanol-free chloroform was then added. The mixture was stirred at −10° for 10 minutes, and for two hours at room temperature, before concentrating under reduced pressure. Methylene chloride was added to the residue, and evaporation under reduced pressure repeated. The amorphous residue was triturated with petroleum ether (b.p. 30°–60° C.) to obtain 200 mg of solid. This solid was dissolved in a mixture of ethyl acetate and water, and adjusted to pH 3.3 with 0.1N HCl. The organic phase was washed with brine, dried ($Na_2SO_4$), decolorized with charcoal, and concentrated under reduced pressure to yield 50 mg of the above product.

EXAMPLE 55

(S,Z)-2-Amino-α-(methoxyimino)-N-[1-[[[[(5-methyl-3-isoxazolyl)amino]sulfonyl]-amino]carbonyl]-2-oxo-3-azetidinyl]thiazole-4-acetamide Sodium Salt
(Compound A)

Injectable Dosage Form

Compound A vials contain 250 mg and 500 mg of Compound A. No excipients are added.

| Item | Ingredient | Amount/Vial |
|---|---|---|
| | 250 mg vial | |
| 1 | Compound A | 250 mg* |
| | 500 mg vial | |
| 1 | Compound A | 500 mg* |

*Additional 6% filling excess is added.

Method of Preparation
1. The drug is filled into sterilized vials under aseptic conditions using a powder filling machine such as a Perry Accofil.
2. The filled vials are stoppered with a rubber stopper and sealed with aluminum seals using appropriate equipment.

Alternate Formulation

| Item | Ingredient | Amount/Vial |
|---|---|---|
| | 250 mg vial | |
| 1 | Compound A | 250 mg* |
| 2 | Lactose, USP | 50 mg |
| 3 | Benzyl Alcohol | 0.3 ml |
| 4 | Water for Injection** | q.s. to 2.0 ml |
| | 500 mg vial | |
| 1 | Compound A | 500 mg* |
| 2 | Lactose, USP | 50 mg |
| 3 | Benzyl Alcohol | 0.3 ml |
| 4 | Water for Injection** | q.s. to 2.0 ml |

*Additional 6% filling excess is added.
**Removed during lyophilization.

Method of Preparation
1. Compound A lactose and benzyl alcohol are dissolved in water for injection and the solution is filtered through a bacterioretentive filter into a sterile container.
2. The solution is subdivided into glass vials under aseptic conditions, the rubber stoppers are positioned and the vials loaded into a lyophilizer and freeze dried using an appropriate cycle.
3. The vials are sealed with aluminum seals under aseptic conditions.

EXAMPLE 56

Minimal Inhibitory Concentrations (μg/mL) values were found for the following compounds

| | | |
|---|---|---|
| Organisms | Z = —SO3Na (Prior Art) | Z = CONNaSO2NH—[isoxazole] |
| E. coli 257 | 1 | 0.5 |
| E. coli 48 | 1 | 0.5 |
| K. pneumoniae | 0.5 | 0.5 |
| E. cloacae 9570A | 2 | 2 |
| P. vulgaris ATCC 6380 | 2 | 0.25 |
| P. mirabilis 503-1136 | 2 | 0.125 |
| P. mirabilis 190 | 1 | 0.125 |
| S. marcescens SM | 8 | 0.5 |
| P. aeruginosa Stone 130 | 32 | 32 |
| P. aeruginosa 503-56 | 32 | 128 |
| S. pyogenes 503-782 | 128 | 16 |
| S. aureus Smith | 64 | 128 |

MIC were obtained in accordance with art recognized procedures.

We claim:

1. A compound of the formula

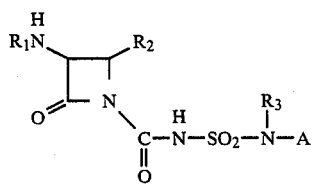

wherein A is

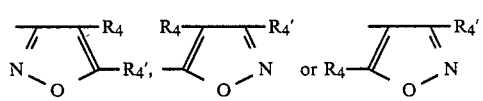

$R_1$ is acyl, $R_2$ is hydrogen, lower alkyl, lower alkoyxcarbonyl or aminocarbonyl, $R_3$ is hydrogen or lower alkyl, and $R_4$ and $R_4'$ are each hydrogen, lower alkyl, lower alkoxy, aryl, aryloxy, or aralkyl and pharmaceutically acceptable salts thereof.

2. A compound as in claim 1, wherein $R_1$ is selected from the group consisting of 2-(2-chloroacetamidothiazol-4-yl)-2-methoxyiminoacetyl, 2-(2-aminothiazol-4-yl)-2-isoproproxyiminoacetyl, 2-(2-aminothiazol-4-yl)-2-methoxyiminoacetyl, 2-furyl-2-methoxyiminoacetyl, 2-(4-hydroxyphenyl)-2-methoxyiminoacetyl, 2-phenyl-2-methoxyiminoacetyl, 2-phenyl-2-hydroxyiminoacetyl, 2-thienyl-2-hydroxyiminoacetyl, 2-thienyl-2-(dichloroacetyloxyimino)acetyl, 2-(5-chloro-2-chloroacetamidothiazol-4-yl)-2-methoxyiminoacetyl, 2-(5-chloro-2-aminothiazol-4-yl)-2-methoxyiminoacetyl, 2-[2-(t-butoxycarbonyl)-2-propoxyimino]-2-(2-sulfoaminothiazol-4-yl)acetyl, 2-[2-(t-butoxycarbonyl)-2-propoxyimino]-2-(2-triphenylmethylaminothiazol-4-yl)acetyl, 2-(2-chloroacetamidothiazol-4-yl)-2-isopropoxyiminoacetyl, 2-methoxyimino-2-(2-sulfoaminothiazol-4-yl)acetyl, 2-(2-mesylaminothiazol-4-yl)-2-isopropoxyiminoacetyl, 2-(2-imino-3-mesyl-4-thiazolin-4-yl)-2-isopropoxyiminoacetyl, 2-[(2-chloroacetamidothiazol-4-yl)-2-[(p-nitrobenzyloxycarbonyl)]methoxyimino]acetyl, 2-[(2-aminothiazol-4-yl)-2-carboxymethyoxyimino]acetyl and 2-[(2-aminothiazol-4-yl)-2-(2-carboxy-2-propoxyimino)]acetyl.

3. A compound as in claim 1 wherein $R_1$ is of the formula:

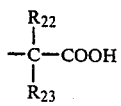

wherein $R^{11}$ is a carbocyclic aromatic group unsubstituted or substituted with halogen, hydroxy, nitro, amino, cyano, trifluoromethyl, $C_1$–$C_4$ alkyl, $C_1$–$C_4$ alkoxy, or $R^{11}$ is a 5-, 6- or 7-membered heterocyclic aromatic group in which the ring contains 1 or 2 nitrogen, oxygen or sulfur atoms and which is unsubstituted or substituted with halogen, hydroxyl, nitro, amino, cyano, trifluoromethyl, $C_1$–$C_4$ alkyl or $C_1$–$C_4$ alkoxy, and $R^{13}$ is hydrogen, lower alkyl, cycloaklyl or substituted alkyl (wherein the alkyl group is substituted with one or more halogen, cyano, nitro, amino, mercapto, alkylthio, carboxyl (including salts thereof), amido, lower alkoxycarbonyl, phenylmethoxycarbonyl, diphenylmethoxycarbonyl, hydroxy lower alkoxyphosphinyl, dihydroxphosphinyl, hydroxy(phenylmethoxy)phosphinyl or dialkoxyphosphinyl substitutents).

4. A compound as in claim 3 wherein $R_{11}$ is

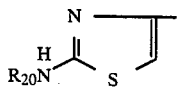

and $R_{20}$ is hydrogen or an amino protecting group.

5. A compound as in claim 3 wherein $R_{13}$ is hydrogen, lower alkyl or a group of the formula

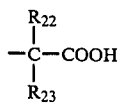

wherein $R_{22}$ and $R_{23}$ are selected from the group consisting of hydrogen and lower alkyl or taken together with the carbon atom to which they are attached form a carbocyclic ring containing 3–7 carbon atoms.

6. A compound as in claim 5 wherein $R_{11}$ is

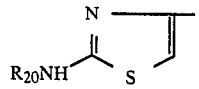

wherein $R_{20}$ is hydrogen.

7. A compound as in claim 4 wherein $R_2$, $R_3$, $R_4$ and $R_4'$ are each hydrogen or lower alkyl.

8. A compound of claim 7 wherein $R_2$, $R_3$, $R_4$ and $R_4'$ are each hydrogen or methyl.

9. A compound as in claim 8 wherein $R_{20}$ is hydrogen.

10. A compound as in claim 9 wherein $R_{13}$ is lower alkyl or a group of the formula

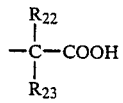

wherein $R_{22}$ and $R_{23}$ are each hydrogen or lower alkyl.

11. A compound as in claim 10 wherein $R_{13}$ is methyl or when $R_{13}$ is

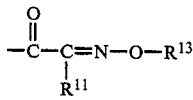

wherein $R_{22}$ and $R_{23}$ are either methyl or hydrogen.

12. A compound as in claim 1 of the formula (S)-N-[1-[[[[(5-lower alkyl-3-isoxazolyl)amino]sulfonyl]amino]carbonyl]-2-oxo-3-azetidinyl]benzeneacetamide and its salts.

13. A compound as in claim 12 wherein the lower alkyl group is methyl.

14. A compound as in claim 1 of the formula S-[1-[[[[(5-lower alkyl-3-isoxazolyl)amino]sulfonyl]amino]carbonyl]-2-oxo-3-azetidinyl]carbamic acid phenyllow-eralkyl ester and its salt.

15. A compound as in claim 14 wherein the lower alkyl groups mentioned therein are both methyl.

16. A compound as in claim 1 of the formula (S,Z)-2-amino-α-(loweralkoxyimino)-N-[1-[[[[(5-lower alkyl-3-isoxazolyl)amino]sulfonyl]-amino]carbonyl]-b 2-oxo-3-azetidinyl]thiazole-4-acetamide and its salt.

17. A compound as in claim 16 wherein the loweralkoxyimino group is methoxyimino and the lower alkyl group is methyl.

18. A compound as in claim 1 of the formula [3S-trans; (Z)]-2-amino-α-(loweralkoxyimino)-N-[4-lower alkyl-1-[[[[(5-lower alkyl-3-isoxazolyl)amino]sulfonyl]amino]carbonyl]-2-oxo-3-azetidinyl]thiazole-4-acetamide and its salt.

19. A compound as in claim 18 wherein both lower alkyl groups thereof are methyl and lower alkoxyimino is methoxyimino.

20. A compound as in claim 1 of the formula 2-[[[1-(2-X-4-thiazolyl)-2-[1-[[[[(5-lower alkyl-3-isoxazolyl)amino]sulfonyl]amino]carbonyl]-2-oxo-3-azetidinyl]amino-2-oxoethylidene]imino]oxy]-2-methylpropanoic acid and its salts wherein X is selected from the group consisting of amino and protected amino.

21. A compound as in claim 20 wherein X is amino.

22. A compound as in claim 1 of the formula 2-[[[1-(2-X-4-thiazolyl)-2-[1-[[[[(5-lower alkyl-3-isoxazolyl)amino]sulfonyl]amino]-2-y-carbonyl]-2-oxo-3-azetidinyl]amino-2-oxoethylidene]imino]oxy](lower alkanoic acid and its salts wherein X is amino or protected amino and y is hydrogen or lower alkyl.

23. A compound as in claim 22 wherein X is amino, the lower alkyl group is methyl, y is methyl and the acid moiety is 2-methyl propanoic acid.

24. A compound as in claim 22 wherein X is amino, the lower alkyl group is methyl and y is hydrogen.

25. A compound as in claim 22 wherein y is hydrogen and the lower alkanoic acid group is acetic acid.

26. A compound as defined in claim 1 of the formula 2-[[[1-(2-amino-4-thiazolyl)-2-[1-[[[[(3-$R_4'$-4-$R_4$-5-isoxazolyl)amino]sulfonyl]amino]carbonyl]-2-oxo-3-azetidinyl]amino-2-oxoethylidene]imino]oxy]-2-Y lower alkanoic acid and its salts wherein Y is selected from the group consisting of hydrogen and lower alkyl and $R_4$ and $R_4'$ are each selected from the group consisting of hydrogen and lower alkyl.

27. A compound as in claim 26 wherein y is methyl the lower alkanoic acid moiety is 2-methyl propanoic acid and $R_4'$ is methyl and $R^4$ is hydrogen.

28. A compound as in claim 26 wherein $R_4'$ is methyl, $R_4$ is hydrogen, Y is hydrogen and the lower alkanoic acid is acetic acid.

29. A compound as in claim 1 of the formula 2-amino(lower alkoxyimino)-N-[1-[[[[(3-$R_4'$-4-$R_4$-5-isoxazolyl)amino]sulfonyl]amino]carbonyl]-2-oxo-3-azetidinyl]thiazole-4-acetamide and its salts wherein $R_4$ and $R_4'$ are selected from the group consisting of hydrogen and lower alkyl.

30. A compound as in claim 29 wherein the lower alkylimino group is methoxyimino, $R_4'$ is methyl and $R_4$ is hydrogen.

* * * * *